(12) United States Patent
Brandenberger et al.

(10) Patent No.: US 7,373,492 B2
(45) Date of Patent: May 13, 2008

(54) BOOT DISK MANAGEMENT UTILITY

(75) Inventors: Philip J. Brandenberger, Montclair, NJ (US); Joseph M. Hedgecock, Old Bethpage, NY (US); T. Gordon Marler, Lyndhurst, NJ (US)

(73) Assignee: Lehman Brothers Inc., New York, NY (US)

( * ) Notice: Subject to any disclaimer, the term of this patent is extended or adjusted under 35 U.S.C. 154(b) by 459 days.

(21) Appl. No.: 10/937,629

(22) Filed: Sep. 9, 2004

(65) Prior Publication Data

US 2006/0047945 A1  Mar. 2, 2006

Related U.S. Application Data

(60) Provisional application No. 60/605,577, filed on Aug. 30, 2004.

(51) Int. Cl.
*G06F 12/00* (2006.01)
(52) U.S. Cl. .............................. 713/1; 713/2; 711/114; 711/165; 711/203
(58) Field of Classification Search .................... 713/1, 713/2; 711/114, 165, 203
See application file for complete search history.

(56) References Cited

U.S. PATENT DOCUMENTS

| | | | | |
|---|---|---|---|---|
| 6,269,431 B1* | 7/2001 | Dunham | ..................... | 711/162 |
| 6,560,701 B1* | 5/2003 | Berstis et al. | .................. | 713/2 |
| 6,760,908 B2* | 7/2004 | Ren | ............................ | 717/173 |
| 6,934,805 B2* | 8/2005 | Hickman et al. | ........... | 711/114 |
| 6,934,881 B2* | 8/2005 | Gold et al. | .................. | 714/15 |
| 6,941,430 B2* | 9/2005 | Jones et al. | .................. | 711/162 |
| 6,996,743 B2* | 2/2006 | Knapp, III | ..................... | 714/6 |
| 7,146,479 B2* | 12/2006 | Li et al. | ...................... | 711/170 |
| 7,185,332 B1* | 2/2007 | Waldin et al. | .............. | 717/170 |
| 2003/0177485 A1* | 9/2003 | Waldin et al. | .............. | 717/169 |
| 2004/0153724 A1* | 8/2004 | Nicholson et al. | ............. | 714/6 |
| 2004/0255283 A1* | 12/2004 | Rudelic et al. | ............. | 717/151 |
| 2005/0091354 A1* | 4/2005 | Lowell et al. | .............. | 709/223 |
| 2006/0005004 A1* | 1/2006 | First et al. | ...................... | 713/2 |
| 2006/0010485 A1* | 1/2006 | Gorman | ......................... | 726/3 |
| 2006/0047942 A1* | 3/2006 | Rothman et al. | .............. | 713/2 |

OTHER PUBLICATIONS

Embedded Systems and Software Resources, "Sun Honors Lehman Brothers For Excellence In UNIX Systems Engineering", Nov. 3, 2003, pp. 1-2.

"Sun Microsystems Recognizes Lehman Brothers for Major Breakthrough and Technology Contributions to Financial Services Community", Press Release, Source: Sun Microsystems, Inc., Oct. 31, 2003, "Lehman Brothers' Technological Advancements Improve Real-Time Upgrades", pp. 1-3.

"Sun Microsystems Recognizes Lehman Brothers for Major Breakthrough and Technology Contributions to Financial Services Community", Press Release, Source: Sun News, Oct. 31, 2003 "Lehman Brothers' Technological Advancements Improve Real-Time Upgrades", pp. 1-2.

"Lehman Brothers Reduces Cost and Improves Performance by Migrating Trading Desk Application From Sun Solaris to Microsoft Windows", Microsoft Financial Services Study, pp. 1-3.

* cited by examiner

*Primary Examiner*—Abdelmoniem Elamin
(74) *Attorney, Agent, or Firm*—Morgan, Lewis & Bockius LLP

(57) ABSTRACT

A computer utility for reducing downtime required for applying patches to a UNIX system, and for allowing changes to the system to be rolled back in the event of problems with a patch.

9 Claims, 11 Drawing Sheets

BOOT DISK MANAGEMENT UTILITY

CROSS REFERENCE TO RELATED APPLICATIONS

This application claims the benefit of U.S. Provisional Patent Application No. 60/605,577, filed Aug. 30, 2004, the entirety of which is incorporated herein by reference.

BACKGROUND OF THE INVENTION

Many critical UNIX systems have the highest availability requirements. These systems have the requirement of being constantly patched to the current level for operating systems to minimize the potential service outage due to a known issue. Patches are often released daily. Unfortunately, these two requirements are contradictory. Patching introduces downtime, often excessive downtime. Current patching state of the art also has weaknesses in the patch removal process, again introducing more downtime on systems that cannot tolerate it.

Eliminating downtime required for applying patches would be ideal but unobtainable due to the nature of the underlying UNIX based operating system and the fact that that many patches require downtime for a reboot. There is a need to minimize downtime to simply the boot time required for this most intrusive of operations.

BRIEF SUMMARY OF THE INVENTION

The current invention addresses the needs present in the prior art.

The present invention is directed to a method and system for reducing downtime of a computer system during system maintenance. An operating environment is run on a primary boot disk while system maintenance is performed on a secondary boot disk. This system maintenance includes identifying patches to be applied to the system, queuing the patches to be applied, and applying the patches. A reboot is performed to the secondary boot disk while the primary boot disk is maintained as a back-up boot environment. Optionally, the primary boot disk may initially be mirrored to the secondary boot disk, or, the operating environment may initially be copied from the secondary boot disk to the primary boot disk.

DETAILED DESCRIPTION

Reference will now be made in detail to the preferred embodiments of the present invention, examples of which are illustrated in the accompanying drawings. It is to be understood that the figures and descriptions of the present invention included herein illustrate and describe elements that are of particular relevance to the present invention, while eliminating, for purposes of clarity, other elements. Those of ordinary skill in the art will recognize that other elements may be desirable and/or required in order to implement the present invention. However, such elements are well known in the art, and because they do not facilitate a better understanding of the present invention, a discussion of such elements is not provided herein.

The invention described herein allows a user to reduce downtime due to maintenance activities. Because only one boot disk has the patch or patches initially installed, the changes can be rolled back to a secondary boot disk. The invention also allows a system to be examined, with only patches applicable to that system being queued for application. The patches are then applied to a Boot Environment ("BE") rather than the live operating system boot disk. The invention further allows a user to create and retain as many BEs as a system has spare local disks.

The invention described herein relates to eliminating downtime required for applying patches to a UNIX system. While the embodiment described herein specifically applies to a Sun Microsystems Solaris/Veritas environment, the invention can be equally applied to all variants of UNIX systems using appropriate variations on the commands described herein. Such variations will be known to those skilled in the art.

The exemplary embodiment of the present invention described herein operates in connection with a system that satisfies the following prerequisites:

1. Sun Microsystems Solaris 2.6, 7, 8, or 9 versions of UNIX.
2. Veritas Volume Manager 3.1, 3.1.1, 3.2, or 3.5.
3. The boot disk of the system must be under Veritas Volume Manager control (i.e., the boot disk must be encapsulated.
4. An unused direct-attached disk, which will be used to create a duplicate of the existing boot disk.
5. The system using the utilities must have access to a patch repository, and any meta-data required to determine which patches can be applied to the system, via NFS, HTTP, etc.
6. The system must have access to Perl 5.6.1 or later.

If this is the first time the utility of the present invention is being used on a system, the procedure for creating the first BE is slightly different than the procedure for creating subsequent ones. This description outlines the process, and discusses when and how the original boot disk should be recycled once proper functioning of the new BE is verified. The concepts and requirements for a BE disk are discussed in detail below.

Figure 1A:
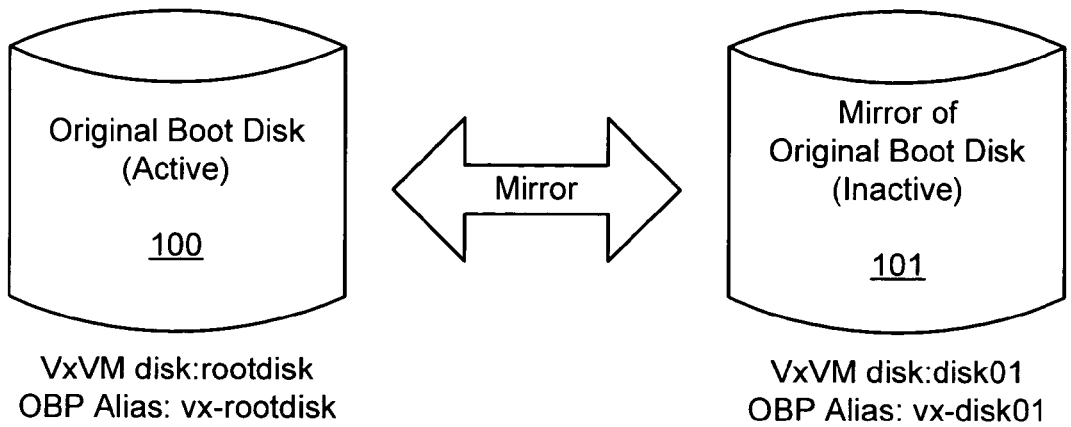
FIG. 1a illustrates a common initial boot disk configuration for an embodiment of the present invention.

FIG. 1a shows a common initial boot disk configuration for an embodiment of the present invention. The primary boot disk 100 is known as rootdisk, whereas the secondary boot disk 101 is known as disk01. The OpenBoot PROM may be configured, depending on the system, with aliases to allow a user to boot to either disk 100 or 101, and to boot to the other disk in case booting to the first one fails. Many systems will have the following definitions:

boot-device=vx-rootdisk vx-disk01
nvramrc=devalias vx-rootdisk . . .
devalias vx-disk01 . . .

For this example, it is assumed that boot disks 101 and 102 are the only two disks available that can be used with the utility. Thus, one of the disks must be freed up. In this case, disk01 will be freed up, which entails the following steps:

Delete the VxVM plexes (mirrors) that reside on boot disk 101, thus breaking the associations between boot disk 100 and boot disk 101.

Delete the VxVM disk media record for disk01, thus freeing it for other uses.

Delete the OBP alias for disk01 and remove it from the boot-device list. Use vxeeprom devunalias . . . AND eeprom boot-device=" . . . "

The procedures to accomplish these steps is as follows:

Use vxprint to get the name of the disk used as a boot disk mirror, as well as the mirror plexes for each volume that is mirrored from the boot disk. In the example below, note the following:

1. rootdisk is the primary boot disk, and is on device c0t0d0s2. disk01 (not all systems use this name) is the mirror boot disk, and is on device c0t1d0s2.
2. Using the -ht option to the vxprint command produces a hierarchical printout of each Veritas Volume: Each Volume (lines starting with v), is composed of one or more Plexes (lines starting with pl), each of which contains a copy of the entire contents of the volume. Each Plex is composed of one or more Subdisks (lines starting with sd).
3. Each of the volumes in the rootdg disk group has a second plex, or mirror, whose subdisks are located on the disk01 disk. Each of these plexes must be removed recursively so that the disk on which their subdisks reside can be removed.

```
vxprint -g rootdg -ht
DG NAME     NCONFIG       NLOG         MINORS         GROUP-ID
DM NAME     DEVICE        TYPE         PRIVLEN        PUBLEN         STATE
RV NAME     RLINK_CNT     KSTATE       STATE          PRIMARY        DATAVOLS       SRL
RL NAME     RVG           KSTATE       STATE          REM_HOST       REM_DG         REM_RLNK
V NAME      RVG           KSTATE       STATE          LENGTH         READPOL        PREFPLEX       UTYPE
PL NAME     VOLUME        KSTATE       STATE          LENGTH         LAYOUT         NCOL/WID       MODE
SD NAME     PLEX          DISK         DISKOFFS       LENGTH         (COL/)OFF      DEVICE         MODE
SV NAME     PLEX          VOLNAME      NVOLLAYR       LENGTH         (COL/)OFF      AM/NM          MODE
DC NAME     PARENTVOL     LOGVOL
SP NAME     SNAPVOL       DCO dg rootdg       default       default      0              1039102710.1025.nj3225c-5
dm rootdisk     c0t0d0s2      sliced       2888           71127179       —
dm disk01       c0t1d0s2      sliced       2888           71121402       —
sd rootdiskPriv —             rootdisk     2120526        2888           PRIVATE        c0t0d0         ENA
v 0             —             ENABLED      ACTIVE         41113359       ROUND          —              fsgen
pl 0-01         0             ENABLED      ACTIVE         41113359       CONCAT         —              RW
sd rootdisk-03  0-01          rootdisk     30013820       41113359       0              c0t0d0         ENA
pl 0-02         0             ENABLED      ACTIVE         41113359       CONCAT         —              RW
sd disk01-03    0-02          disk01       22727763       41113359       0              c0t1d0         ENA
v rootvol       —             ENABLED      ACTIVE         2120526        ROUND          —              root
pl rootvol-01   rootvol       ENABLED      ACTIVE         2120526        CONCAT         —              RW
sd rootdisk-B0  rootvol-01    rootdisk     2120525        1              0              c0t0d0         ENA
sd rootdisk-02  rootvol-01    rootdisk     0              2120525        1              c0t0d0         ENA
pl rootvol-02   rootvol       ENABLED      ACTIVE         2120526        CONCAT         13             RW
sd disk01-01    rootvol-02    disk01       0              2120526        0              c0t1d0         ENA
v swapvol       —             ENABLED      ACTIVE         20607237       ROUND          —              swap
pl swapvol-01   swapvol       ENABLED      ACTIVE         20607237       CONCAT         —              RW
sd rootdisk-01  swapvol-01    rootdisk     2123414        20607237       0              c0t0d0         ENA
pl swapvol-02   swapvol       ENABLED      ACTIVE         20607237       CONCAT         —              RW
sd disk01-02    swapvol-02    disk01       2120526        20607237       0              c0t1d0         ENA
v var           —             ENABLED      ACTIVE         7283169        ROUND          —              fsgen
pl var-01       var           ENABLED      ACTIVE         7283169        CONCAT         —              RW
sd rootdisk-04  var-01        rootdisk     22730651       7283169        0              c0t0d0         ENA
pl var-02       var           ENABLED      ACTIVE         7283169        CONCAT         —              RW
sd disk01-03    var-02        disk01       22727763       7283169        0              c0t1d0         ENA
```

Remove each volume's mirror plex. In this case the plexes to remove are highlighted above: rootvol-02, swapvol-02, var-02, and 0-02. The commands below also remove the subdisks contained in each plex.
    # vxplex -g rootdg -o rm dis rootvol-02
    # vxplex -g rootdg -o rm dis swapvol-02
    # vxplex -g rootdg -o rm dis var-02
    # vxplex -g rootdg -o rm dis 0-02
Remove the mirror disk 101 (disk01) from the rootdg disk group. This frees this disk up for use as a BE.
    # vxdg -g rootdg rmdisk disk01
Remove the alias for disk vxdisk01.
    #/etc/vx/bin/vxeeprom devunalias vx-disk01
Remove the vx-disk01 alias from the OpenBoot PROM boot-device list, if it is there.
    # eeprom boot-device="vx-rootdisk"

Figure 1B:
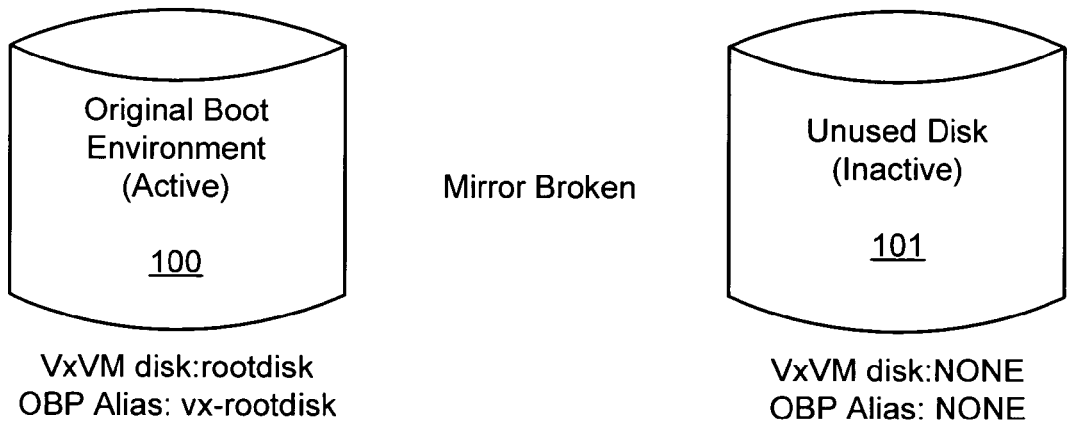
FIG. 1b illustrates a boot disk configuration for an embodiment of the present invention after mirrors have been broken.

FIG. 1*b* shows the result of taking these actions. At this point, a BE can be created on the unused disk 101 (the device name for this disk is c0t1d0s2) using the be-create command. In this example, the BE will be given the name vmupgrade:

be_create --BE=vmupgrade --device=c0t1d0

The system may be configured to detect that this is the first time the utility is being run on this host, and may create a special BE configuration record for the original boot disk 100, named "orig". This is simply a placeholder, and no other changes are required to the original boot disk. The system may also make changes to the OBP settings to make them consistent with the original disk's new BE name. This step may also be accomplished manually.

The be_create program may produce output giving a user the status, and may log more detailed information in /var/log/BE.log. The resulting BE may also be bootable as part of the creation procedure.

Figure 1C:
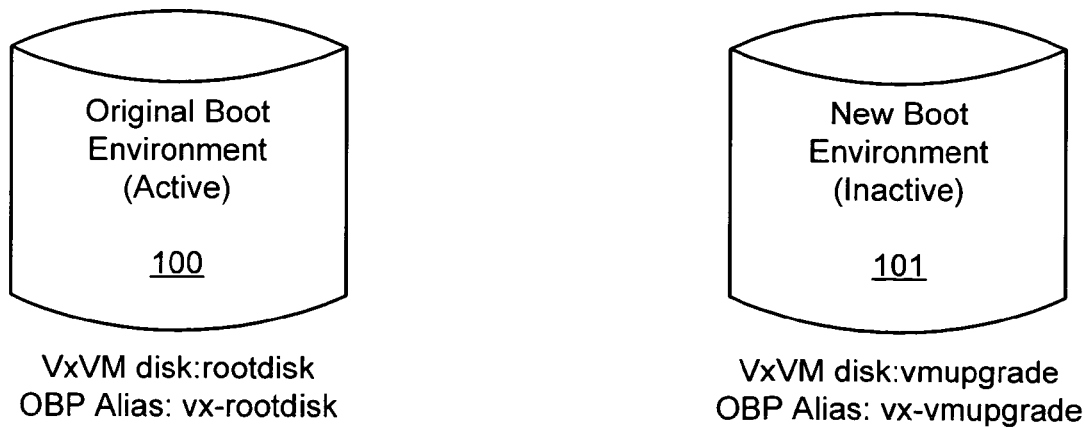
FIG. 1c illustrates a boot disk configuration for an embodiment of the present invention after a Boot Environment has been created on an inactive disk.

The result of these actions is shown in FIG. 1*c*. Note that the OBP alias for the new BE is:

vx-Bename.

At this point, the new BE can be mounted (at /.lbbe.v-mupgrade/) and changes can be made to it that will be seen when the system is booted to the new BE. The BE can be mounted with the following command:

be_mount --BE=vmupgrade

At this point, maintenance can be performed on the new BE, which is safe because disk 101 is inactive, while boot disk 100 is currently active. Modifications may be handled by various utility scripts, and these scripts have their own documentation that varies from release to release. Once the desired modifications have been made, the BE must be unmounted before attempting to boot to it:

be_umount --BE=vmupgrade

The system can now be booted to the new BE at the user's convenience:

reboot -- vx-vmupgrade

Depending on the system, rebooting twice in quick succession may be required. This may also be documented in the modification procedure and may appear as part of the upgrade script output. This is because the installation of the new VxVM product requires the first reboot to occur with the Volume Manager disabled, because entirely new VxVM devices have to be created by the new loadable kernel modules that come with the new Volume Manager. Immediately after this boot, the Volume Manager can be re-enabled and rebooted again. When the system comes back up, the Volume Manager will be active again. This expands the "reboot" command above to be:

reboot -- vx-vmupgrade

<Wait for System to Reboot and log in as Root> cd /etc cp vfstab.vm vfstab cp system.vm system reboot -- vx-vmupgrade

<System will Reboot with the Volume Manager Enabled>

Figure 1D:
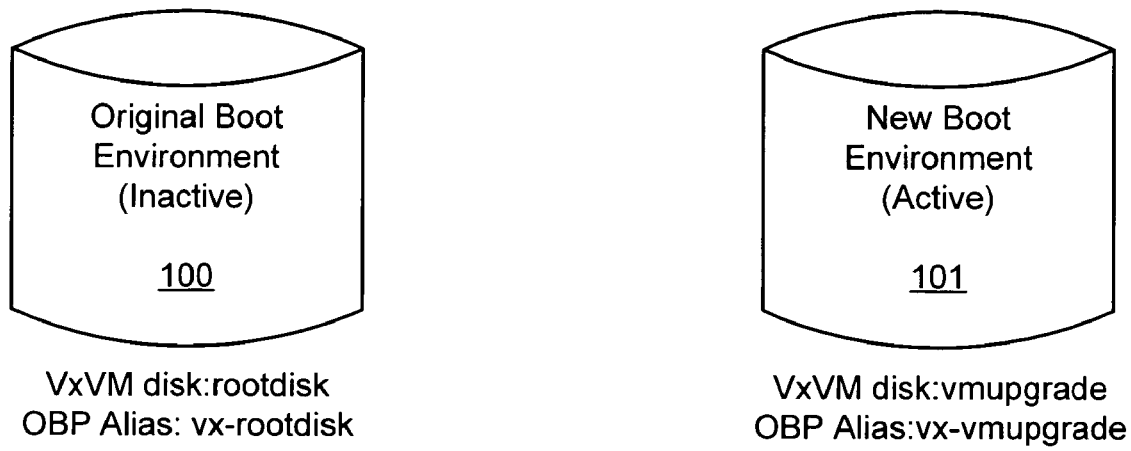
FIG. 1d illustrates a boot disk configuration for an embodiment of the present invention after the system has been rebooted to a new Boot Environment.

The results of taking these actions are shown in FIG. 1*d*.

Now the system is running on the new BE, and the original BE is inactive. However, to maintain this, a manual change is needed to the OpenBoot PROM settings. At this point, an OBP alias exists for both disks, but only one of the disks will ever be automatically booted from the original disk unless a manual change is made to the OBP settings. In the preferred embodiment, this set up is intentional, as there is always a chance that the new BE may not work properly on any given system, and it is preferable to require explicitly booting to the new BE until it can be ensured that it boots properly. At this point, the OBP boot-device setting should look as follows:

boot-device=vx-rootdisk vx-rootmirror

Since the vx-rootmirror was destroyed earlier, it may be removed. Also, a user wanting to boot to the new BE by default will need to add its alias (vx-vmupgrade) to the front of the OBP boot-device setting with a command such the following:

eeprom boot-device="vx-vmupgrade vx-rootdisk"

At this point, when a standard reboot, init 6, or other system restart command is issued, the system will attempt to boot to the new BE disk; if this fails, the original boot disk will be used.

In the preferred embodiment, it is typical to run the system this way for at least a few days before recycling the original boot disk to be used as a mirror of the new BE. The reasons for doing this are as follows:

The new BE may not be suitable for the system for any number of reasons, e.g., old applications that depend upon old bugs in the system that have been patched in the new BE, unusual hardware configurations may not act well with the changes on the new BE, etc. These problems may present themselves immediately, or not for a few days. If the original BE is destroyed right away, the opportunity to roll back changes and trying again is lost.

Even if a disk failure occurs on the new BE, the change made to the OBP will ensure that it will boot back to the original disk, and will at least be up and running while maintenance is performed on the other disk. Exposure to this kind of problem will be limited to the amount of time the original boot disk is maintained.

Once the new BE's stability has been verified, the original boot disk 100 may be recycled so that it can be used as a mirror for the new BE. This requires deleting the "orig" BE that was specially created around the original boot disk 100. All references to the original boot disk must be deleted from the OBP. Although it is possible to accomplish this in one command, for this example, the following steps will be used:

```
# be_delete --BE=orig
<Save a Copy of the Device Pointed to by the OBP Alias
vx-rootdisk in /tmp/recycled-device>
# /etc/vx/bin/vxeeprom devalias vx-rootdisk>/tmp/recycled-
device
#/etc/vx/bin/vxeeprom devunalias vx-rootdisk
# eeprom boot-device="vx-vmupgrade"
```

Figure 1E:
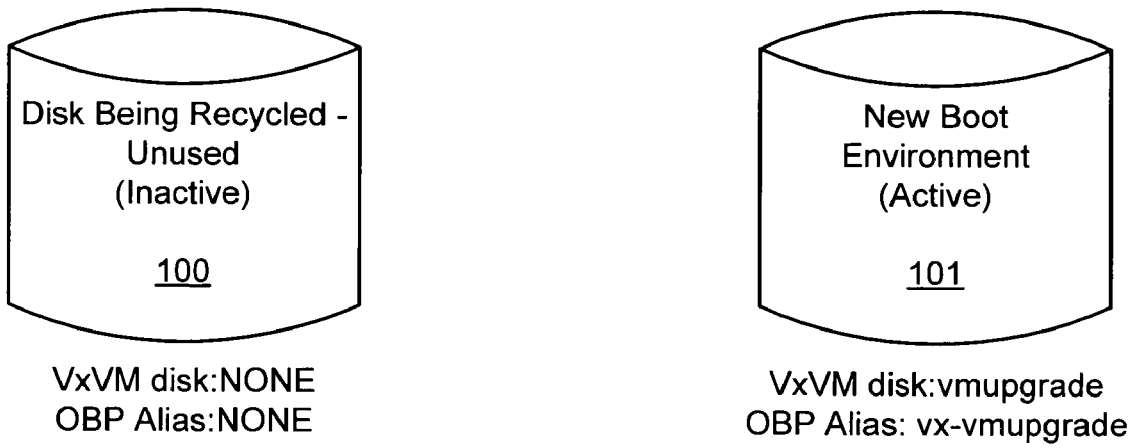
FIG. 1e illustrates a boot disk configuration for an embodiment of the present invention after references to the original boot disk have been deleted.

The results of running these commands are shown seen in FIG. 1e. The system can now only boot to disk 101 with the OBP alias vx-vmupgrade.

Figure 1F:
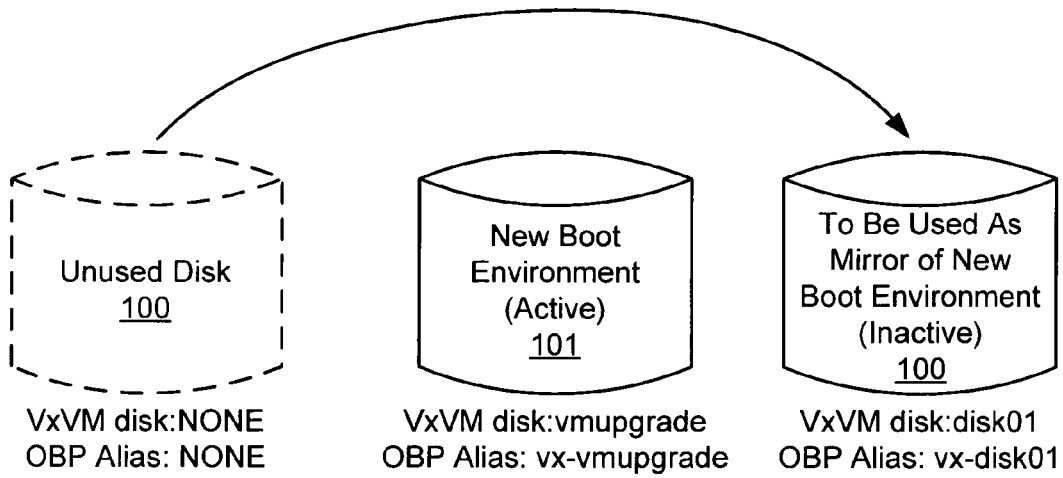
FIG. 1f illustrates the recycling of a boot disk in an embodiment of the present invention.

The original boot disk 100 is now ready to for recycling. In this example, the standard Veritas Volume Manager techniques are used to carry out these actions, which are illustrated in FIG. 1f:

Set up the disk being recycled as part of the rootdg disk group, and name it disk01.

Mirror each of the volumes on disk 101 named vmupgrade to disk01.

Create an OBP alias for the boot block on disk01, which we preserved earlier in /tmp/recycled-device:
```
    # /etc/vx/bin/vxeeprom devalias vx-disk01 'cat /tmp/
    recycled-device'
```

Set up the OBP boot-device setting to allow booting from either of the disks.
```
    # eeprom boot-device="vx-vmupgrade vx-disk01"
```

Figure 1G:
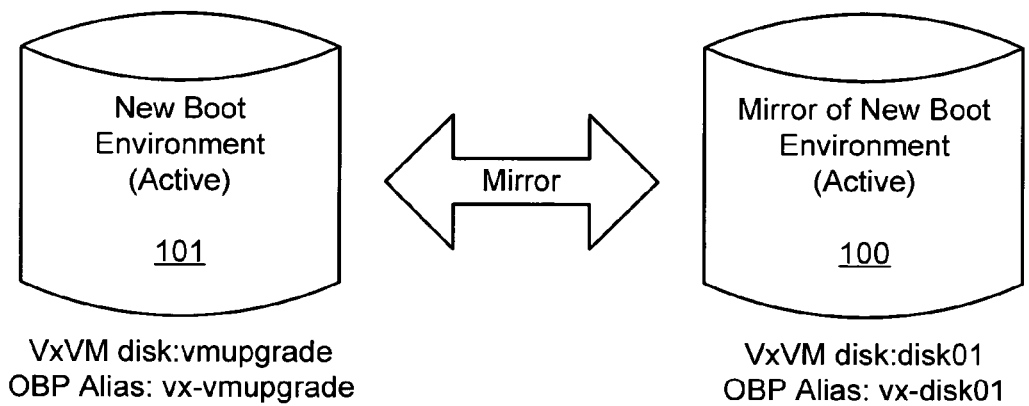
FIG. 1g illustrates a boot disk configuration for an embodiment of the present invention after a boot disk has been recycled.

The final result of these commands is shown in FIG. 1g, i.e., a fully mirrored, redundant boot disk, with full OBP support for booting to either, manually or automatically.

Figure 1H:
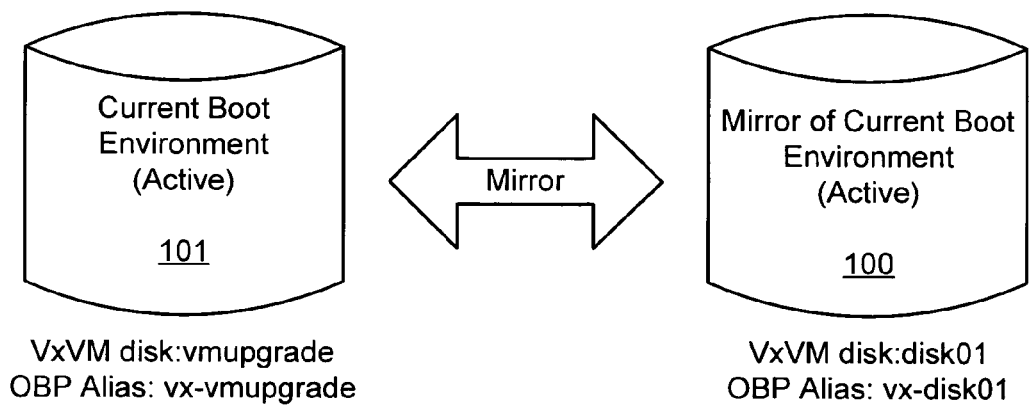
FIG. 1h illustrates a boot disk configuration for an embodiment of the present invention after a boot disk has been recycled.

Subsequent BE creations on a system will now be considered. At the end of the last example, the state of the boot disk mirrors is displayed in FIG. 1h. A new BE will be created to apply exemplary production patches, which will be referred to herein as patch0903. It will also be assumed that these are the only two disks available in the system.

Thus, one of these disks must be freed up for use as the new BE. In this case, disk01 will be freed up, requiring the following steps:

Delete the VxVM plexes (mirrors) that reside on disk01, thus breaking the associations between rootdisk and disk01.

Delete the VxVM disk media record for disk01, thus freeing it for other uses Delete the OBP alias for disk01 and remove it from the boot-device list. Use vxeeprom devunalias . . . AND eeprom boot-device=" . . . "

The procedure to accomplish these steps is as follows:

Use vxprint to get the name of the disk used as a boot disk mirror, as well as the mirror plexes for each volume that is mirrored from the boot disk. In the example below, note the following:

1. vmupgrade is the primary boot disk, and is on device c0t1d0s2 after the last example was completed. disk01 is the mirror boot disk, and is on device c0t0d0s2.

2. Using the -ht option to the vxprint command produces a hierarchical printout of each Veritas Volume: Each Volume (lines starting with v), is composed of one or more Plexes (lines starting with p1), each of which contains a copy of the entire contents of the volume. Each Plex is composed of one or more Subdisks (lines starting with sd).

3. Each of the volumes in the rootdg disk group has a second plex, or mirror, whose subdisks are located on the disk01 disk. Each of these plexes must be removed recursively so that the disks on which the subdisks reside can be removed.

```
vxprint -g rootdg -ht
DO NAME      NCONFIG      NLOG       MINORS       GROUP-ID
DM NAME      DEVICE       TYPE       PRIVLEN      PUBLEN       STATE
RV NAME      RLINK_CNT    KSTATE     STATE        PRIMARY      DATAVOLS    SRL
RL NAME      RVG          KSTATE     STATE        REM_HOST     REM_DO      REMRLNK
V NAME       RVG          KSTATE     STATE        LENGTH       READPOL     PREFPLEX    UTYPE
PL NAME      VOLUME       KSTATE     STATE        LENGTH       LAYOUT      NCOL/WID    MODE
SD NAME      PLEX         DISK       DISKOFFS     LENGTH       (COL/)OFF   DEVICE      MODE
SV NAME      PLEX         VOLNAME    NVOLLAYR     LENGTH       (COL/)OFF   AM/NM       MODE
DC NAME      PARENTVOL    LOOVOL
SP NAME      SNAPVOL      DCO dg rootdg        default        default      0           1039102710.1025.nj3225c-5
dm disk01        c0t0d0s2       sliced       2888        71127179     —
dm vmupgrade     c0t1d0s2       sliced       2888        71121402     —
v 0              —              ENABLED      ACTIVE      41113359     ROUND —     fsgen
p1 0-02          0              ENABLED      ACTIVE      41113359     CONCAT      —           RW
sd disk01-03     0-02           disk01       30013820    41113359     0           c0t0d0      ENA
p1 0-01          0              ENABLED      ACTIVE      41113359     CONCAT      —           RW
sd vmupgrade-03  0-01           vmupgrade    22727763    41113359     0           c0t1d0      ENA
v rootvol        —              ENABLED      ACTIVE      2120526      ROUND       —           root
p1 rootvol-02    rootvol        ENABLED      ACTIVE      2120526      CONCAT      —           RW
sd disk01-02     rootvol-02     disk01       0           2120525      1           c0t0d0      ENA
p1 rootvol-01    rootvol        ENABLED      ACTIVE      2120526      CONCAT      —           RW
sd vmupgrade-01  rootvol-01     vmupgrade    0           2120526      0           c0t1d0      ENA
v swapvol        —              ENABLED      ACTIVE      20607237     ROUND       —           swap
p1 swapvol-02    swapvol        ENABLED      ACTIVE      20607237     CONCAT      —           RW
sd disk01-01     swapvol-02     disk01       2123414     20607237     0           c0t0d0      ENA
p1 swapvol-01    swapvol        ENABLED      ACTIVE      20607237     CONCAT      —           RW
sd vmupgrade-02  swapvol-01     vmupgrade    2120526     20607237     0           c0t1d0      ENA
```

Remove each volume's mirror plex. In this case, the plexes to remove are highlighted above: rootvol-02, swapvol-02, and 0-02. The commands below also remove the subdisks contained in each plex.

```
# vxplex -g rootdg -o rm dis rootvol-02
# vxplex -g rootdg -o rm dis swapvol-02
# vxplex -g rootdg -o rm dis 0-02
```
Remove the mirror disk (disk01) from the rootdg disk group. This frees this disk up for use as a BE.
```
# vxdg -g rootdg rmdisk disk01
```
Remove the alias for disk vxdisk01.
```
#/etc/vx/bin/vxeeprom devunalias vx-disk01
```
Remove the vx-disk01 alias from the OpenBoot PROM boot-device list, if it's there.
```
# eeprom boot-device-"vx-vmupgrade"
```

Figure 1I:
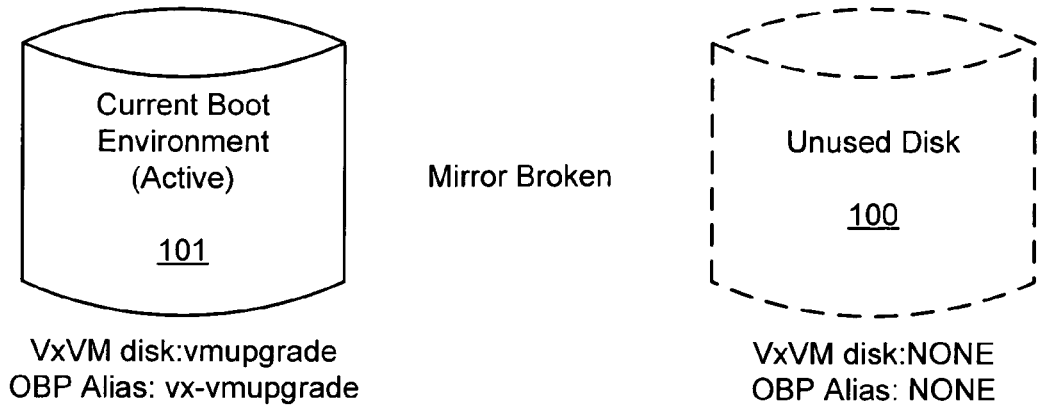
FIG. 1i illustrates a boot disk configuration for an embodiment of the present invention after a boot disk has been freed up for use as a new Boot Environment.

FIG. 1*i* shows the result of taking these actions. At this point, a bootable BE can be created on the unused disk 100 (the device name for this disk is c0t0d0s2) using the be_create command. As discussed earlier, the new BE will be named patch0903:

```
# be_create --BE=patch0903 --device=c0t0d0
```

Figure 1J:
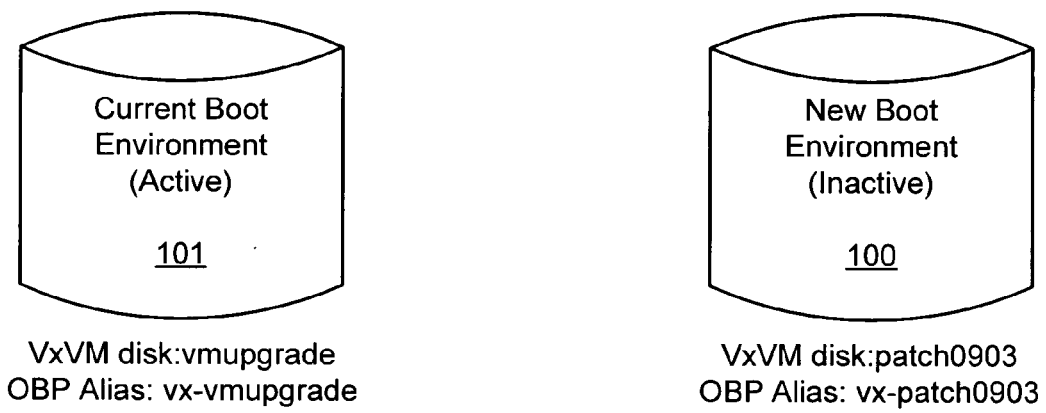
FIG. 1j illustrates a boot disk configuration for an embodiment of the present invention where a new Boot Environment is created on an unused disk.

The result of these actions is shown in FIG. 1*j*. Note that the new BE has an OBP alias of vx-patch0903.

At this point, the new BE can be mounted (at /.lbbe-.patch0903/) and changes can be made to it that will be seen when the system is booted to it. The BE can be mounted with the following command:

```
# be_mount --BE=patch0903
```

Modifications to this BE can be made, treating /.lbbe.patch0903/ as though it was the /directory. Once the desired modifications have been made, the BE must be unmounted before attempting to boot to it:

```
# be_umount --BE=patch0903
```

The new BE can be booted to at any time of the user's choosing:

```
# reboot -- vx-patch0903
```

Figure 1K:
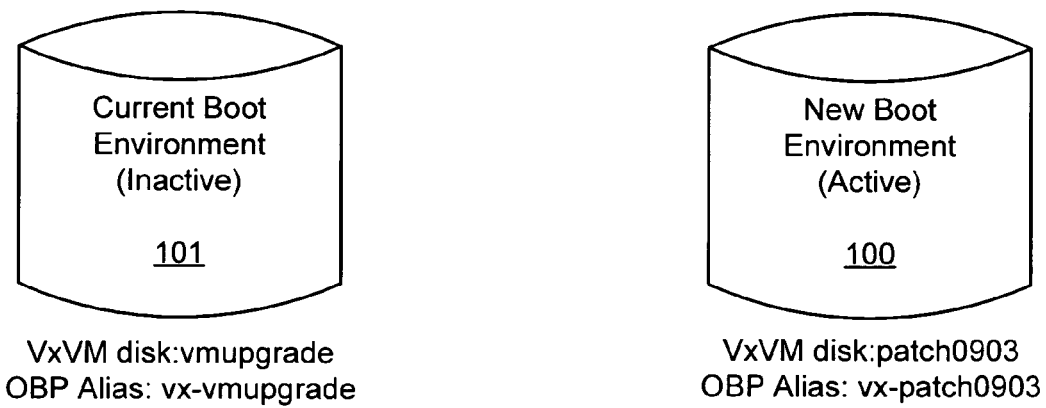
FIG. 1k illustrates a boot disk configuration for an embodiment of the present invention after a system has been rebooted to a modified Boot Environment.

The results of taking these actions are seen in FIG. 1*k*.

Now the system is running on the new BE, and the older BE is inactive. However, to maintain this, a manual change is needed to the OpenBoot PROM settings. At this point, an OBP alias exists for both disks, but only one of the disks will ever be automatically booted from—the original disk—unless a manual change is made to the OBP settings. This set up is intentional, as there is always a chance that the new BE may not work properly on any given system, and it is preferable to require explicitly booting to the new BE until the user is sure that it boots properly. At this point, the OBP boot-device setting should look like this: boot-device=vx-vmupgrade If the new BE is to be booted to by default, its alias (vx-patch0903) must be added to the front of the OBP boot-device setting:

```
# eeprom boot-device="vx-patch0903 vx-vmupgrade"
```

Now, when a standard reboot, init 6, or other system restart command is issued, the system will attempt to boot to the vx-patch0903 disk; if this fails, the vx-vmupgrade boot disk will be used.

The system may be allowed to run this way for at least a few days before recycling the original boot disk to be used as a mirror of the new BE. The reasons for doing this are as follows:

The new BE may not be suitable for the system for any number of reasons, e.g., old applications that depend upon old bugs in the system that have been patched in the new BE, unusual hardware configurations may not act well with the changes on the new BE, etc. These problems may present themselves immediately, or not for a few days. If the original BE is destroyed right away, the opportunity to roll back changes and try again is lost.

It is not required to have a mirror of the new BE immediately. If a problem is presented with the new BE (other than a disk failure), it may be caused by a problem with the new BE, and the user may want the original BE to fall back on.

Even if a disk failure occurs on the new BE, the change made to the OBP will ensure that the system may be booted back to the original disk, which will at least be up and running while maintenance is performed on the other disk. Exposure to this kind of problem will be limited to the amount of time the original boot disk is maintained.

Once the new BE has been determined to be stable over time, the user may want to recycle the vmupgrade boot disk, so that it can be used as a mirror for the new BE. To do this requires that the "vmupgrade" BE be upgraded. All references to the original boot disk must also be removed from the OBP, but the name of that device should be saved in a file (/tmp/recycled-device in this example), since a new alias for it will be created shortly thereafter. Although it is possible to accomplish the procedure of this paragraph with a single command, in this example the following steps are taken:

```
# be_delete --BE=vmupgrade
```

<Save a Copy of the Device Pointed to by the OBP Alias vx-vmupgrade in /tmp/recycled-device>

```
# /etc/vx/bin/vxeeprom devalias vx-vm upgrade>/tmp/recycled-de vice
#/etc/vx/bin/vxeeprom devunalias vx-vmupgrade
# eeprom boot-device="vx-patch0903"
```

Figure 1L:
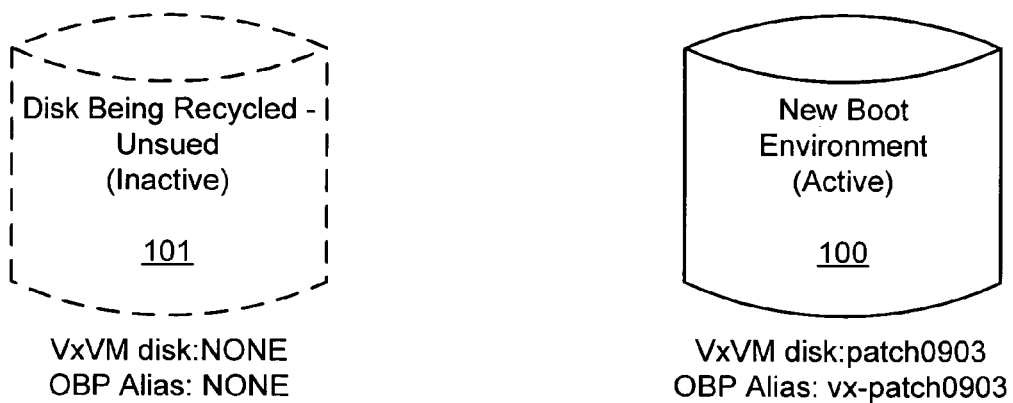
FIGS. 1l and 1m illustrate a boot disk configuration for an embodiment of the present invention after a system has been rebooted to a modified Boot Environment.
Figure 1M:
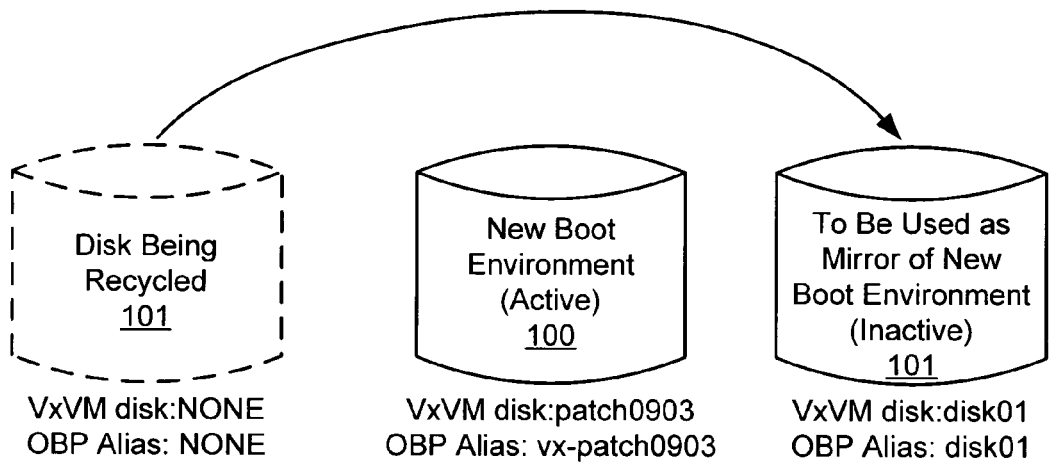

This is illustrated in FIGS. 1*l* and 1*m*. The system can now only boot to the disk with the OBP alias vx-patch0903.

The former vmupgrade boot disk is now ready for recycling. In this example, the standard Veritas Volume Manager techniques are used to carry out these actions:

Set up the disk being recycled as part of the rootdg disk group, and name it disk01.

Mirror each of the volumes on the disk named patch0903 to disk01.

Create an OBP alias for the boot block on the new disk01, which was preserved earlier in /tmp/recycled-device:

```
# /etc/vx/bin/vxeeprom devalias vx-disk01 'cat /tmp/recycled-device'
```

Set up the OBP boot-device setting to allow booting from either of the disks.

```
# eeprom boot-device="vx-patch0903 vx-disk01"
```

Figure 1N:
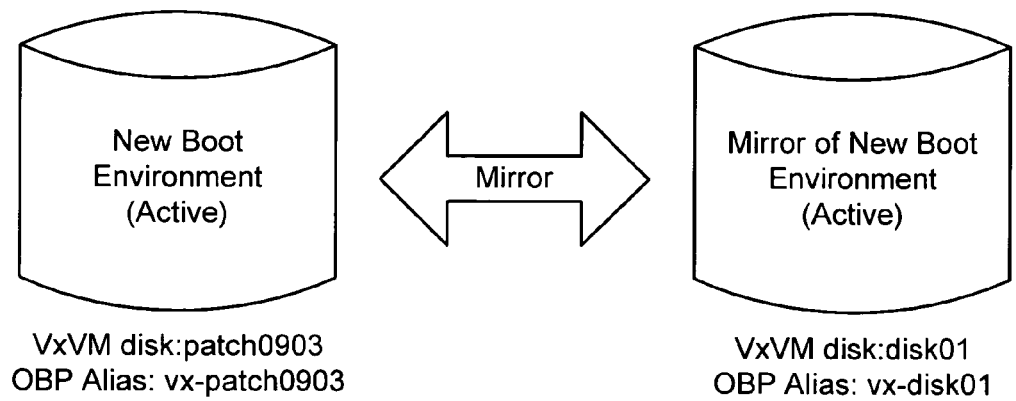
FIG. 1n illustrates a boot disk configuration for an embodiment of the present invention with fully mirrored, redundant boot disks.

The final result of these commands is shown in FIG. 1*n*, i.e., a fully mirrored, redundant boot disk, with full OBP support for booting to either, manually or automatically.

It is advantageous that a system have a minimum of three boot disks available, to support the creation of a new BE, while maintaining a mirror of the original boot disk. The present invention will support the use of any number of BE disks, but requires that any boot disk mirror be broken before a new BE can be created. Once a BE is created, the mirror can be restored.

Creating a new BE requires:
1. A locally attached disk to be used as the new BE.
2. The disk which will be used as the new BE must not be under Veritas Volume Manager control prior to creating the BE.
3. The existing boot disk must not be mirrored during the BE creation. Any existing mirror must be destroyed prior to the BE creation. After the creation is complete, the mirror can be recreated.
4. A unique name for the new BE. The name is only required to be unique on a per host basis. The name should be descriptive, as many BEs can be created on a single machine, only limited by the number of free locally attached disks.

The term locally attached disk means any type of disk that is not on the Storage Area Network. This means that any internal drive (including FC-AL drives in systems such as the Sun V880), drives in external drive bays (such as the Sun D130), or drives in external drive arrays that are directly connected with a SCSI cable can be used as BE disks. Note that many smaller systems, such as Sun Netras, have only two internal drives, and these drives are usually mirrors of one another. In these cases, the present invention can still be used, but the mirror will have to be destroyed and used as the new BE. Once the new BE is validated to work well, the original BE can be removed, and used as the new mirror. If a system has only one disk, the present invention cannot be used on it.

In another embodiment of the present invention, the disk device c0t1d0s2 (an internal 36 GB disk on this Sun E420) is to be used as a new BE. First, it is confirmed that this disk is not currently under Veritas Volume Manager control, by using the vxdisk list command, and noting that the "DISK" and "GROUP" columns have dashes (-) in them:

| # vxdisk list | | | | |
|---|---|---|---|---|
| DEVICE | TYPE | DISK | GROUP | STATUS |
| c0t0d0s2 | sliced | rootdisk | rootdg | online |
| c0t1d0s2 | sliced | — | — | online |
| c1t10d0s2 | sliced | disk01 | snapdg | online |
| c1t11d0s2 | sliced | vm35 | rootdg | online |
| c2t16d0s2 | sliced | — | — | error |
| c2t16d81s2 | sliced | — | — | error |
| c2t16d123s2 | sliced | disk01 | ricks_dg | online |
| c2t16d124s2 | sliced | — | — | online |
| c2t16d125s2 | sliced | — | — | online |
| c2t16d126s2 | sliced | — | — | online |
| c2t16d127s2 | sliced | — | — | online |
| c2t16d128s2 | sliced | — | — | online |
| c2t16d129s2 | sliced | — | — | online |
| c2t16d130s2 | sliced | — | — | online |
| c3t17d0s2 | sliced | — | — | error |
| c3t17d81s2 | sliced | — | — | error |
| c3t17d123s2 | sliced | — | — | online |
| c3t17d124s2 | sliced | — | — | online |
| c3t17d125s2 | sliced | — | — | online |
| c3t17d126s2 | sliced | — | — | online |
| c3t17d127s2 | sliced | — | — | online |
| c3t17d128s2 | sliced | — | — | online |
| c3t17d129s2 | sliced | — | — | online |
| c3t17d130s2 | sliced | — | — | online |

Next, a name for the new BE has to be chosen, in this example, patch1202.

Finally, in this embodiment of the present invention, templates are used to automatically provide a guideline for sizing the / and /local/0 filesystem volumes, as well as the swap volume. The values in the templates are based upon the size of the drive on which the new BE is being created. At this time, the /usr and /var filesystems (and any other filesystems that are located on the current boot disk only) are collapsed into the / filesystem, but /local/0 is kept separate.

Under normal circumstances, collapsing the filesystems is perfectly acceptable, as this is the recommended configuration from Sun and Veritas since Solaris 2.5 was released. As an added protection, in a preferred embodiment of the present invention, UFS logging is automatically turned on for all UFS filesystem on newly created BEs, for Solaris 7 and later. UFS logging can actually improve filesystem performance, and will prevent the need for an fsck of these filesystems if the system should crash in the future.

With this information, the command to actually create the new BE can now be issued:

be_create --BE=patch1202 --device=c0t1d0

The first time be_create is run on a system, the current boot disk is given a default BE name of orig. However, in the described embodiment, no OpenBoot PROM alias is created for this BE.

By default, a newly created BE is bootable. There creation process also creates an OpenBoot PROM alias to help boot to the new BE. The alias created will be of the form: vx-{BEname}. Thus, if the new BE's name is patch1202, the OpenBoot PROM alias for it would be: vx-patch1202.

Creating a BE only makes it bootable and creates an alias—it does not change the default boot disk. This is done to prevent the loss of the original default boot device, and to make it easy to boot back to the original BE, if this is needed. To change the default boot device to the BE just activated, a command, such as the one following, can be run inside the Solaris OS:

eeprom boot-device=vx-patch1202

Alternatively, the following command can be run at the OpenBoot PROM prompt:

ok setenv boot-device vx-patch1202

Once created, a BE can be mounted at a predetermined mount point, so that its contents can manually be altered. This mount point is of the form: /.lbbe.{BEname}. Thus, if the BE name is patch1202, it will be mounted under /.lbbe.patch1202. Note that all of the filesystems that are listed in /etc/vfstab on that BE disk and are physically located on the BE disk are mounted, not just the root (/) filesystem. Some reasons for mounting an inactive BE are:
1. To edit configuration files.
2. To Add/Remove packages.
3. To Remove patches (The be upgrade patching application command automatically mounts/unmounts a BE to perform its work, so a user doesn't have to manually mount a BE to perform patch application).

Example: Mount the BE Named Patch1202 be_mount --BE=patch1202

The BE is now mounted under /.lbbe.patch1202

A package that supports the use of the -R <alternate roots option can be installed on a mounted BE. Note that some packages do not support the use of the -R <alternate root> option. Example: Install the package LBabc on the BE named patch1202—note that this BE has to be mounted before this action can be performed:

pkgadd -R /.lbbe.patch1202 LBabc

A package that supports the use of the -R <alternate roots option can be removed from a mounted BE. Note that some packages do not support the use of the -R <alternate roots> option. Example: Remove the package LBabc from the BE named patch1202—note that this BE has to be mounted before this action can be performed:

pkgrm -R /.lbbe.patch1202 LBabc

If a BE is mounted and administrative work is carried out on it, it must be subsequently unmounted to make it bootable again.

Example: Unmount the BE Named Patch1202 be_umount --BE=patch1202

The BE is now unmounted and the /lbbe.patch1202 directory is removed. Note that the BE mounting process makes the BE unbootable until the BE is unmounted again.

It is sometimes desirable to obtain a list of the patches that could be applied to a BE before actually applying them.

Example: Get a Patch Report for the BE Named Patch1202.

be_patch --BE=patch1202 --report

Note that the be_patch command automatically mounts the named BE before producing a patch report for a BE. It also automatically unmounts the BE before completing.

Certain patches are available for application to a BE via the PatchManager framework. The be-patch tool examines the BE and compares it against the latest approved list of patches for the OS version loaded on the BE and the characteristics of the BE's loaded packages. A patch list customized for this BE is constructed, and can be applied to the BE. It is also possible to obtain a patch report for the BE with the --report option.

Example: Apply the Latest Patches for the BE Named Patch1202, and Get a Patch Report as well.

be_patch --BE=patch1202 --apply --report

Note that the be_patch command automatically mounts the named BE before applying patches to a BE. It also automatically unmounts the BE before completing.

If a BE no longer serves a purpose, or needs to be destroyed to make room for a new BE to be created, it can be destroyed.

Example: Delete the BE Named Patch1202.

be_delete --BE=patch1202

The status of all BEs in a system can be determined by running the be_status command:

| # be_status BE_Name | DG_Name | Disk_Group_ID | CURRENT BOOTABLE DEVICE(s) | | |
|---|---|---|---|---|---|
| orig | rootdg | 1039102710.1025.nj3225c-5 | NO | YES | c0t0d0 |
| vm35 | rootdg | 1039106150.1193.nj3225c-5-orig | YES | YES | c1t11d0 |

FIGS. 2a through 2f are flow charts illustrating preferred embodiments of methods of the present invention.

Figure 2A:
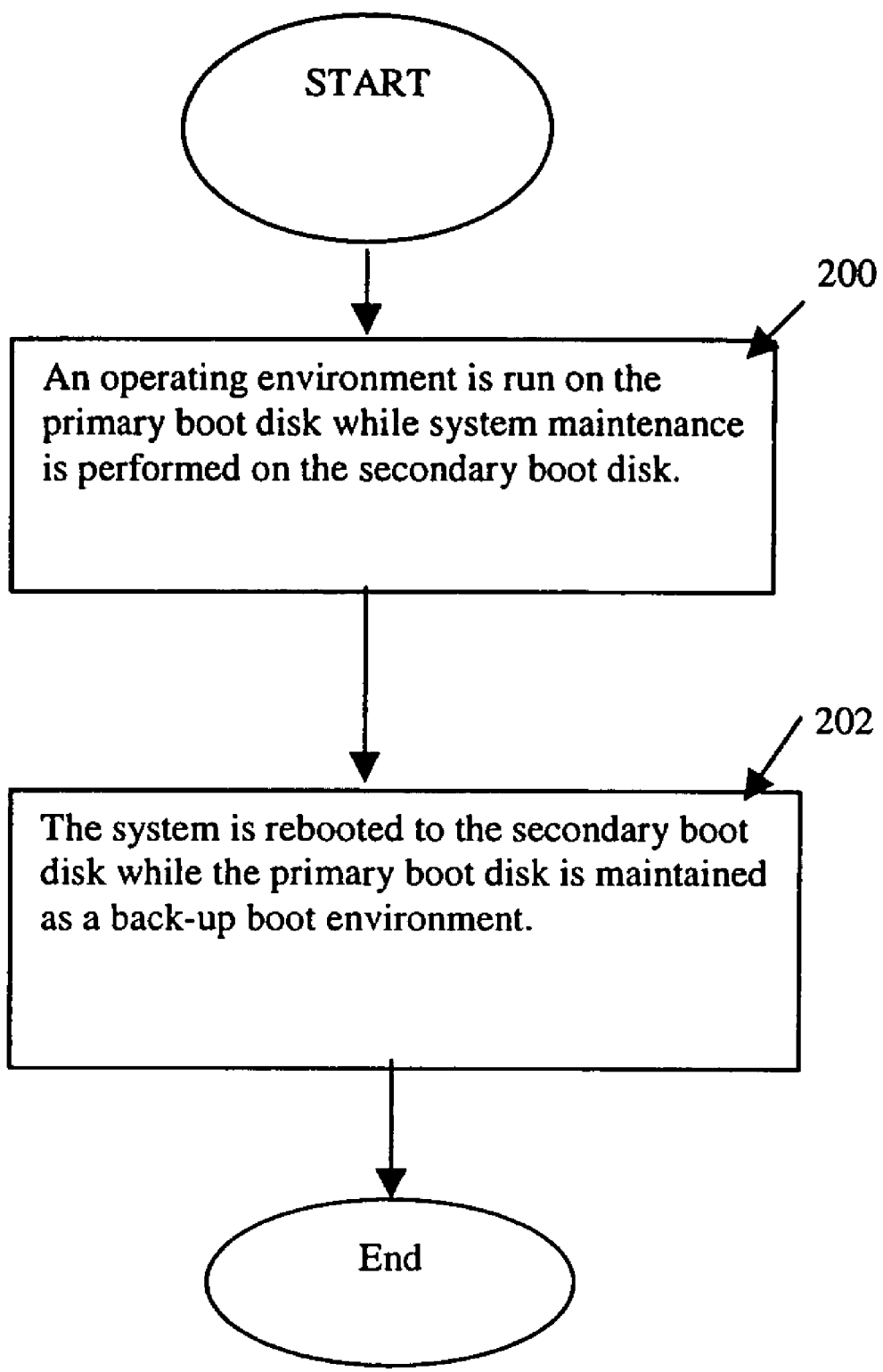
FIG. 2a is a flow chart of the operations that are performed in an embodiment of the present invention.

Referring to FIG. 2a, the operating environment is run on the primary boot disk while system maintenance is performed on the secondary boot disk (step 200). The system is rebooted to the secondary boot disk while the primary boot disk is maintained as a back-up BE (step 202).

Figure 2B:
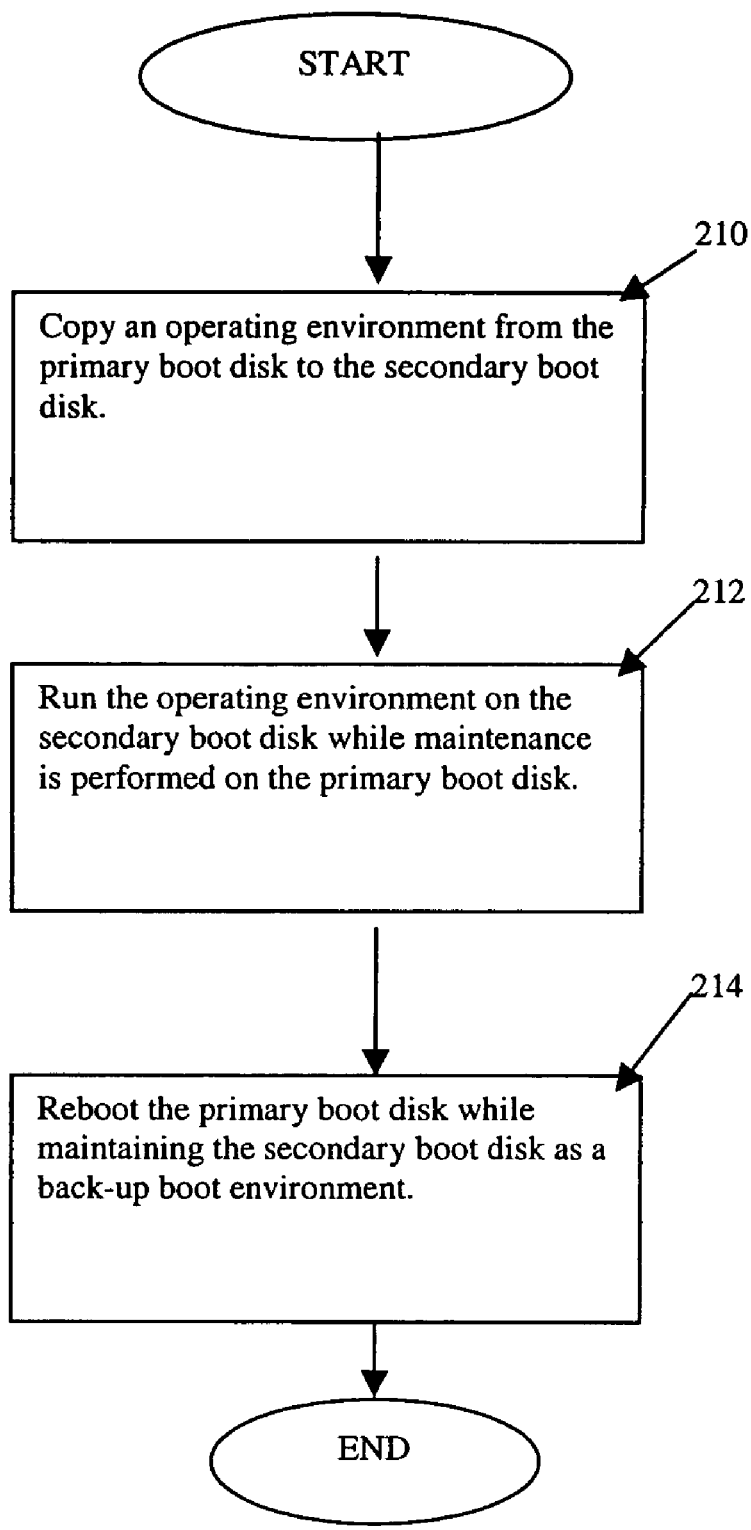
FIG. 2b is a flow chart of the operations that are performed in an embodiment of the present invention.

Referring to FIG. 2b, an operating environment is copied from the primary boot disk to the secondary boot disk (step 210). The operating environment is run on the secondary boot disk while system maintenance is performed on the primary boot disk (step 212). The primary boot disk is rebooted while the secondary boot disk is maintained as a back-up BE (step 214).

Figure 2C:
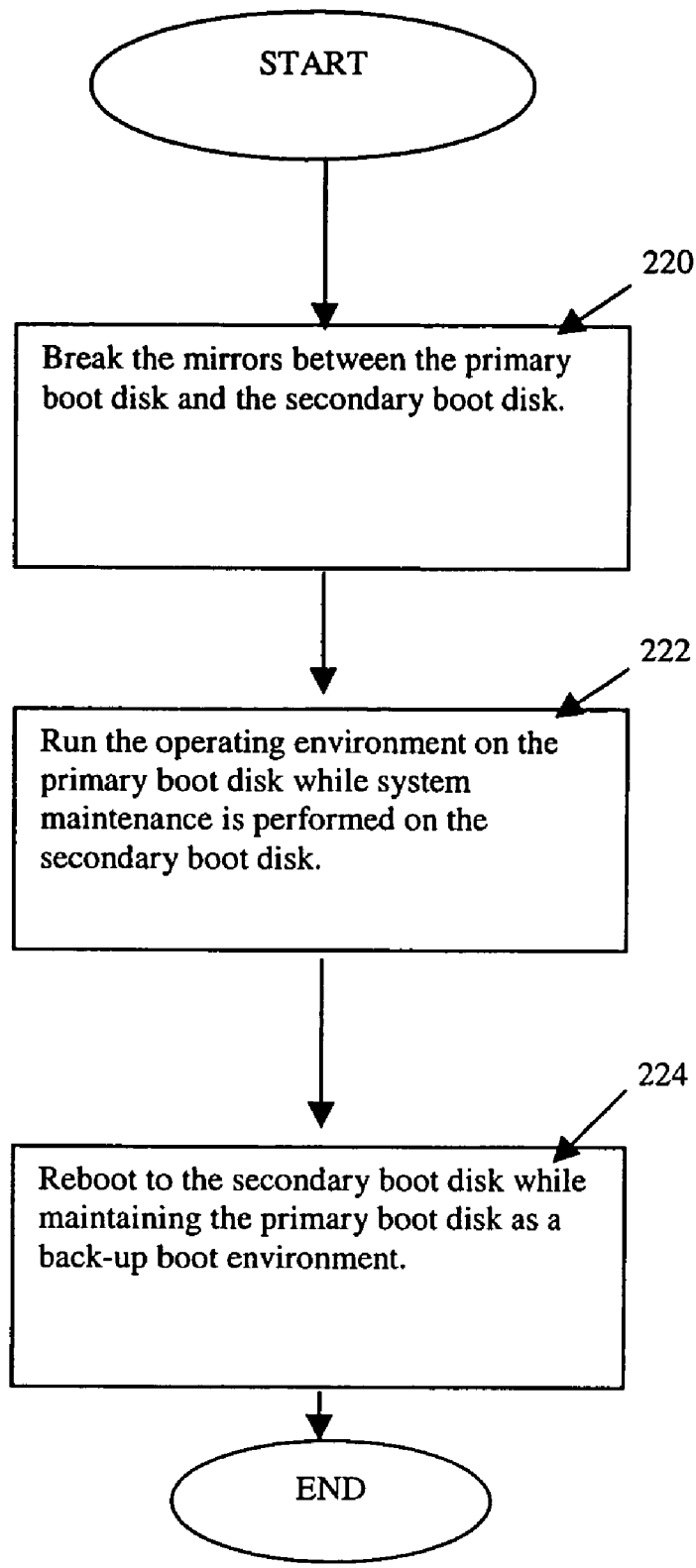
FIG. 2c is a flow chart of the operations that are performed in an embodiment of the present invention.

Referring to FIG. 2c, mirrors are broken between the primary boot disk and the secondary boot disk (step 220). The operating environment is then run on the primary boot disk while system maintenance is performed on the secondary boot disk (step 222). The system is rebooted to the secondary boot disk while the primary boot disk is maintained as a back-up BE (step 224).

Figure 2D:
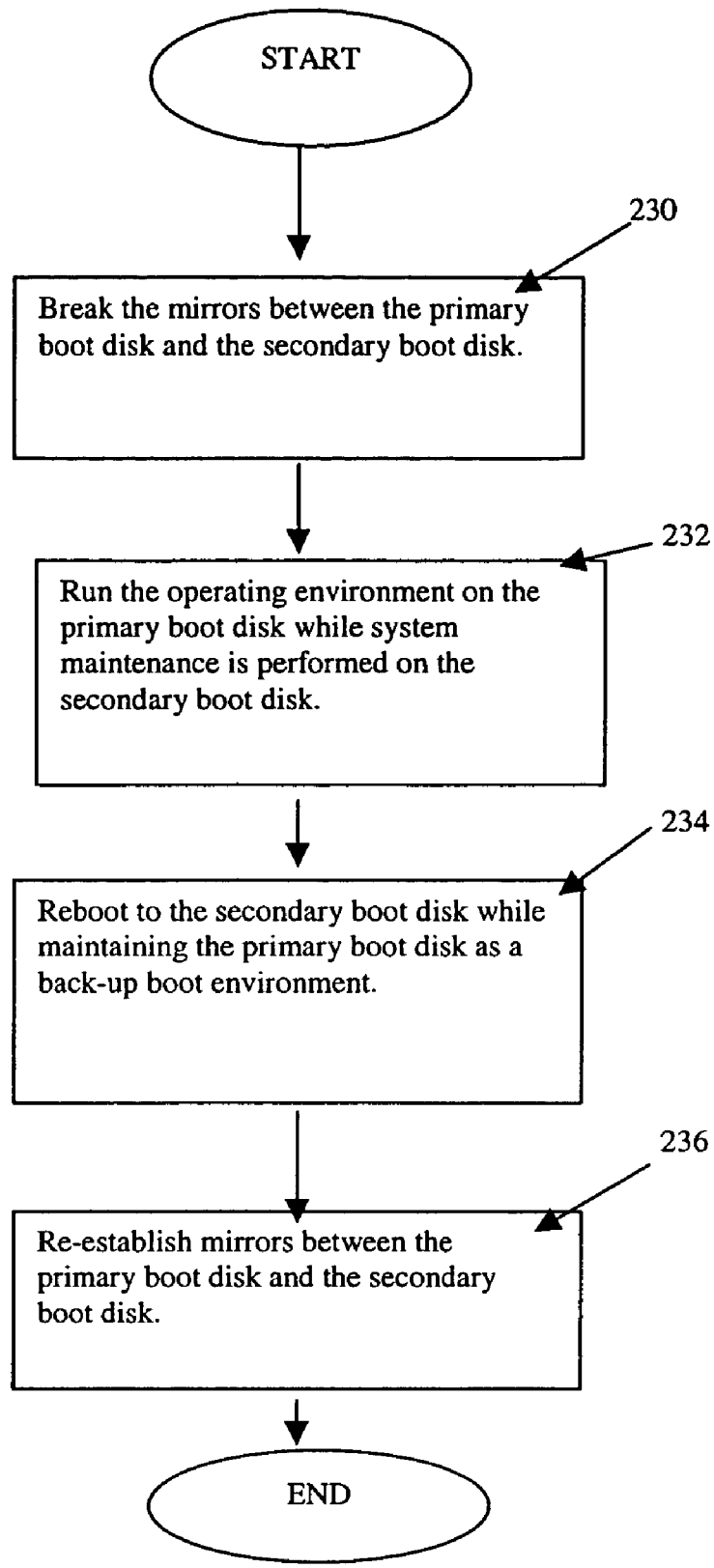
FIG. 2d is a flow chart of the operations that are performed in an embodiment of the present invention.

Referring to FIG. 2d, steps 230, 232, and 234 correspond to steps 220, 222, and 224, respectively, with additional step 236, re-establishing mirrors between the primary boot disk and the secondary boot disk.

Figure 2E:
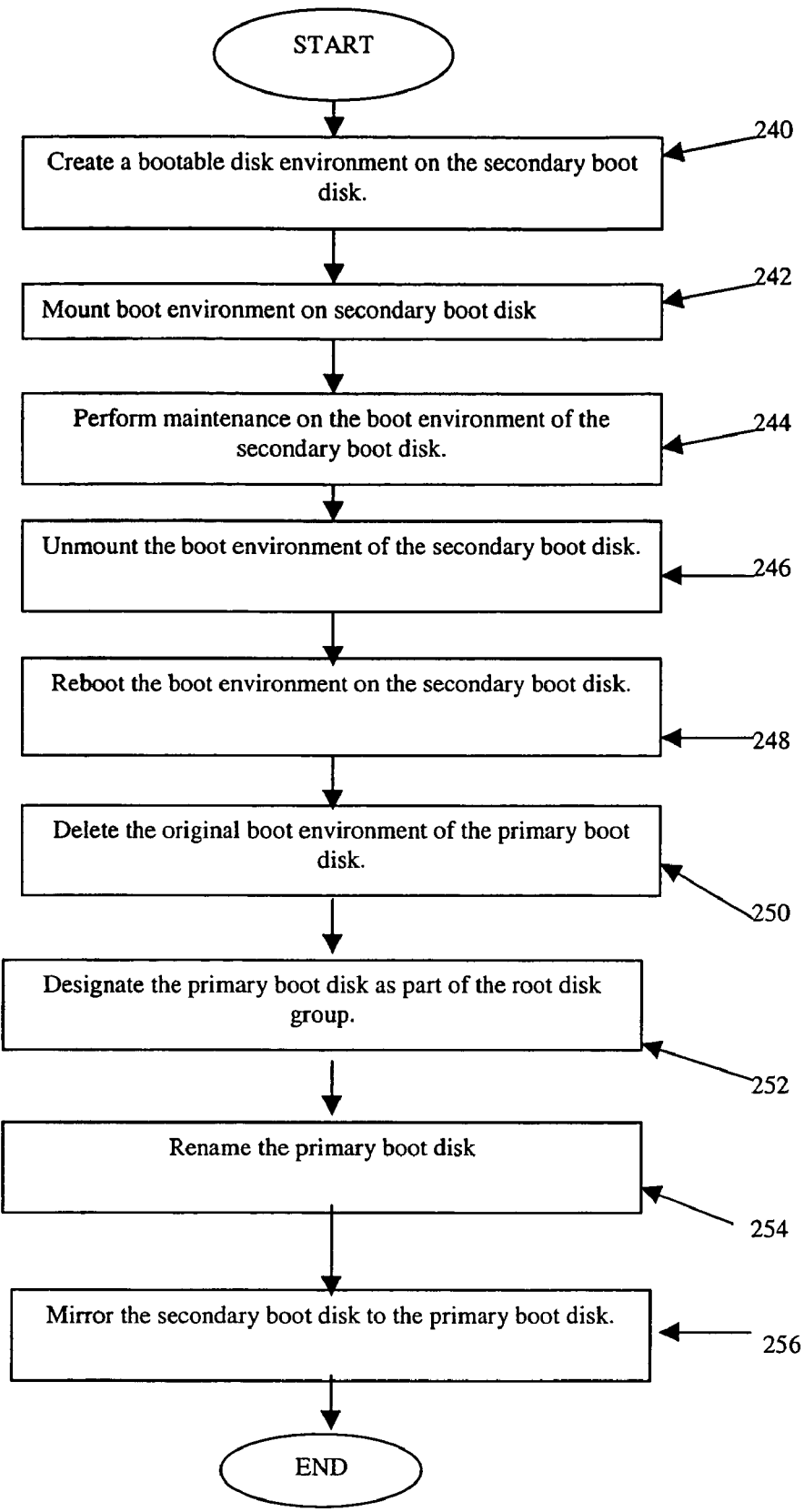
FIG. 2e is a flow chart of the operations that are performed in an embodiment of the present invention.

Referring to FIG. 2e, a bootable BE is created on the secondary boot disk (step 240). The BE of the secondary boot disk is mounted (step 242). System maintenance is performed on the boot environment of the secondary boot disk (step 244). The BE of the secondary boot disk is unmounted (step 246). The BE is booted on the secondary boot disk (step 248). The original BE of the primary boot disk is deleted (step 250). The primary boot disk is designated as part of the root disk group (step 252). The primary boot disk is renamed (step 254) and the secondary boot disk is mirrored to the primary boot disk (step 256).

Figure 2F:
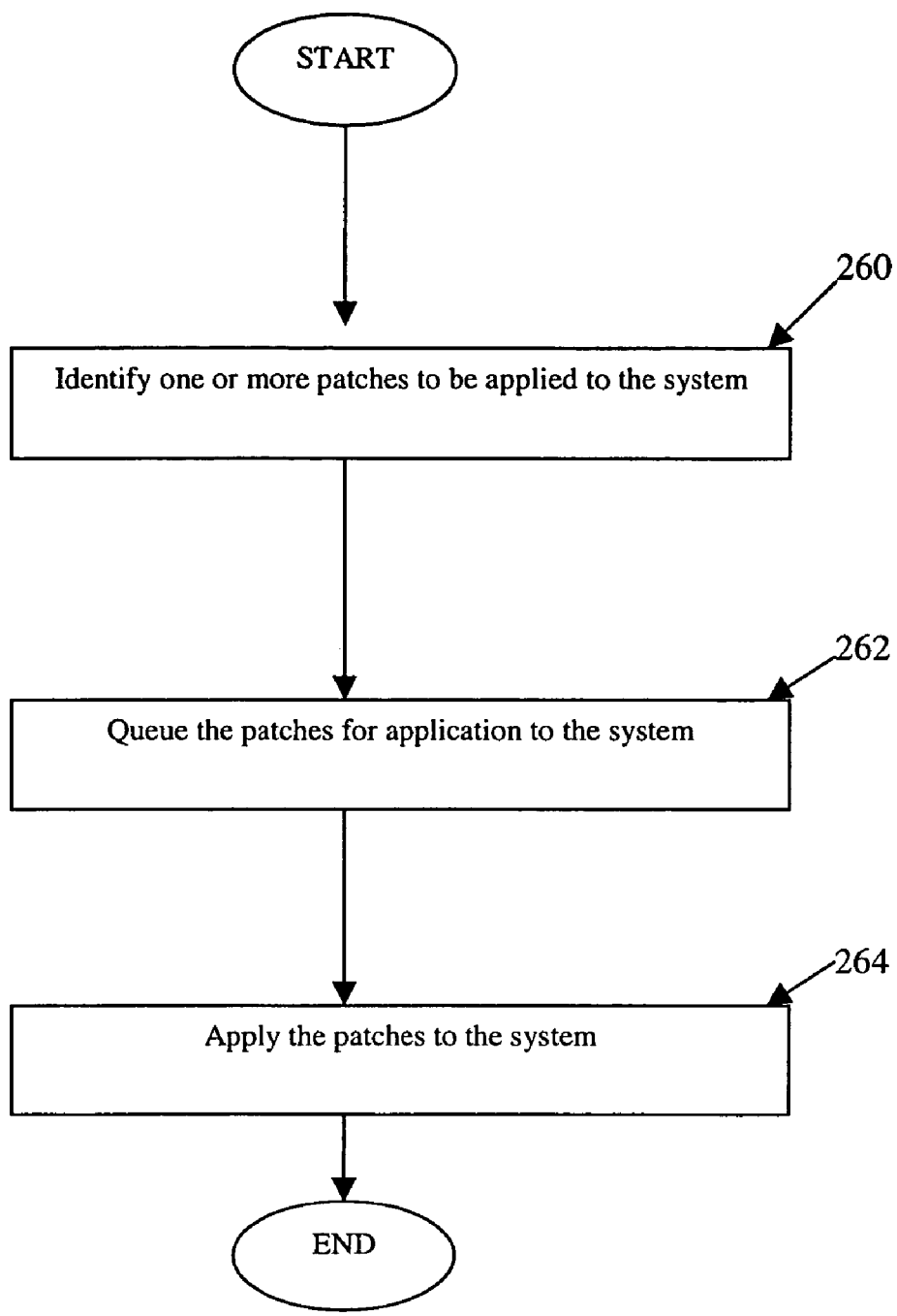
FIG. 2f is a flow chart of the operations that are performed in connection with system maintenance in an embodiment of the present invention.

Referring to FIG. 2f, the steps involved in system maintenance for an embodiment of the present invention are illustrated. These steps comprise identifying one or more patches to be applied to the system (step 260), queuing the patches for application to the system (step 262), and applying the patches to the system (step 264). Each time system maintenance is performed in connection with the methods illustrated in FIGS. 2a-e, the steps of FIG. 2f may be included.

Following is a list of commands used in the present invention:

be_Create: Used to create a new BE on an existing disk. The resulting BE is bootable.

Prerequisites:

The system must already be under Veritas Volume Manager control.

The boot disk must already be encapsulated or initialized.

Any existing mirrors of the existing boot disk must be removed.

Options:

--BE=BEname

Gives a descriptive name (BEname) of the user's choosing to the new BE being created. Note that if this is the first time a BE is being created on the machine in question, a BE record will be created for the existing boot disk as well, and it will be given a predetermined BE name (or prompt the user to give it one). In this way, a user can refer to both the new and the original BEs by name.

--device=device

Gives the name of the disk device on which to create the new BE. This device can be in any of the following forms: /dev/[r]dsk/c0t0d0s2, c0t0d0, c0t0d0s2.

--no_checksum

By default, be create performs an MD5 checksum on all files copied from the current BE to the new BE. This makes sure that no corruption took place during the copy. If a BE creation is intended only for test use, then this option can decrease the time it takes to create a new BE. be_status: Lists the status of all existing BEs that exist on this host. This is the only way to get a list of all BE names.

Options:
None
be_mount: Mounts the specified BE at /lbbe.BEname/. Allows users to manually mount a BE so that package or patch adds/removes can be performed manually with the -R /.lbbe.BEname option to pkgadd/pkgrm/patchadd/patchrm commands.
NOTE: Make sure to unmount a BE (using be_umount) before trying to boot to it—otherwise the boot attempt will fail.

Options:
--BE=BEname
Gives the name of the BE the user wishes to mount.
be_umount: Unmounts the specified BE. Deletes the mount point upon completion.

Options:
--BE=BEname
Gives the name of the BE the user wishes to unmount.
be_delete: Deletes the specified BE, freeing the disk that contained it for other use.

Options:
--BE=BEname
Gives the name of the BE the user wishes to delete.
be_patch: Currently, this utility is used to examine the current patch level of the specified BE, and provide a detailed report of patches that are:
1. Current on this BE.
2. Are totally new to this host (no version of the patch has ever been applied).
3. Updates to patches that are currently applied.
The utility will also optionally apply any necessary patches to bring the BE up to the latest patch level.

Options:
--BE=BEname
Gives the name of the BE the user wishes to apply patches to.
--report
Gives a detailed patch report.
--apply
Makes the utility apply the latest patch updates to this BE, in dependency order.
--list I --listprod
List the Production Patch Databases that have been approved by Unix Engineering.
--listdev
List the Development Patch Databases.
--patchdb_rev <tag>
Selects a particular Patch Database to check out of the central Patch DB CVS repository. The list of tags can be seen with the --list and --listdev options.
--checksum etc
Produces a report after patching that describes all configuration files under /etc on the new BE that have been:
Added by the patches that were applied
Deleted by the patches that were applied
Modified by the patches that were applied
-jumpstart
When running be-patch non-interactively, this option will prevent the Patch Pro Database parser from displaying a countdown of patch entries being parsed. This keeps the output of the non-interactive run of be-patch clean.
Following is a list of utilities used with the present invention:
fc_hba_util (/usr/LBBE/bootdiskmanager/utils/fc_hba_util)

This utility serves 3 purposes:
1. Upgrade the Emulex FibreChannel HBA driver to the latest version.
2. Verify that the configuration of the (latest) HBA driver is correct, and correct it if it is not.
3. Upgrade the Emulex FibreChannel HBA firmware on a live system, one card at a time, while ensuring that PowerPath is fully able to restore all paths through each HBA as its firmware is upgraded. Only then will the utility proceed to the next HBA card.
This utility will only operate if the latest approved versions of VxVM, VxFS, and PowerPath are already in place on the BE or live boot disk on which this utility is asked to operate.

Options:
--BE=BEname
If given, the specified BE's driver will be checked to see if it needs an upgrade. If so, one will be done, and the configuration of the original driver (usually just the WWPN target numbers) will be copied into the new driver configuration file. The new driver configuration file will also be edited to conform to the EMC SAN fabric recommendations for that driver version (as they vary from version to version). If the driver is already at the proper version, its configuration will be compared against the EMC SAN fabric recommendations for that driver version, and any necessary corrections will be made.
If no options are given, the utility will assume that it is operating on the live boot disk, and will not attempt a driver upgrade. If the latest driver version is loaded though, it will validate and correct its configuration, if needed. The utility will then verify that the latest firmware is loaded on each card, and will upgrade it if needed. This has to be done in real-time, and causes a reset of each card. The utility verifies that all LUNs seen through that card are again visible to both the HBA driver and PowerPath (if in use) before proceeding to the next card's firmware upgrade.

vx35upgrade (/usr/LBBE/bootdiskmanager/bin/vx35upgrade)
This utility is a shell script in this release, and requires a BE name on which to operate. It will not operate on a live boot disk. If necessary, it will upgrade to the latest VxVM, VxFS, VEA, and PowerPath products. If these products are not already installed, it will not install them. They must already be installed when this utility is invoked.

What is claimed is:
1. A method, comprising the steps of:
mirroring a primary boot disk to a secondary boot disk;
breaking the mirrors between the primary boot disk and the secondary boot disk, the secondary boot disk being a complete mirror of the primary boot disk at the time the mirrors are broken;
performing maintenance on the secondary boot disk, the secondary boot disk being a complete mirror of the primary boot disk, while running an operating environment on the primary boot disk, the maintenance including identifying one or more patches to be applied to the computer system, queuing the patches for application, and applying the patches; and
rebooting to the secondary boot disk while maintaining the primary boot disk as a back-up boot environment.
2. The method of claim 1 further comprising the step of re-establishing the mirrors between the secondary boot disk and the primary boot disk.

3. The method of claim 1 further comprising the steps of:
creating a bootable boot environment on the secondary boot disk;
booting the boot environment on the secondary boot disk;
deleting an original boot environment of the primary boot disk;
designating the primary boot disk as part of a root disk group;
renaming the primary boot disk; and
mirroring the secondary boot disk to the primary boot disk.

4. A computer system, comprising:
a primary boot disk; and
a secondary boot disk,
wherein
the primary boot disk is mirrored to the secondary boot disk,
the mirrors are broken between the primary boot disk and the secondary boot disk, the secondary book disk being a complete mirror of the primary boot disk at the time the mirrors are broken,
maintenance is performed on the secondary boot disk, the secondary boot disk being a complete mirror of the primary boot disk, while running an operating environment on the primary boot disk, and
the secondary boot disk is rebooted while the primary boot disk is maintained as a back-up boot environment, the maintenance including identifying one or more patches to
be applied to the computer system, queuing the patches for application, and applying the patches.

5. The computer system of claim 4, wherein the secondary boot disk is mirrored to the primary boot disk after the system is rebooted to the secondary boot disk.

6. The computer system of claim 4, wherein a bootable boot environment is created on the secondary boot disk, the boot environment is booted on the secondary boot disk, an original boot environment is deleted from the primary boot disk, the primary boot disk is designated as part of a root disk group, the primary boot disk is renamed, and the secondary boot disk is mirrored to the primary boot disk.

7. A computer program product including a computer readable medium having stored thereon computer executable instructions that, when executed on a computer, configure the computer to perform a method comprising the steps of:
mirroring a primary boot disk to a secondary boot disk;
breaking the mirrors between the primary boot disk and the secondary boot disk, the secondary boot disk being a complete mirror of the primary boot disk at the time the mirrors are broken;
performing maintenance on the secondary boot disk, the secondary boot disk being a complete mirror of the primary boot disk, while running an operating environment on the primary boot disk, the maintenance including identifying one or more patches to be applied to the computer system, queuing the patches for application, and applying the patches; and
rebooting to the secondary boot disk while maintaining the primary boot disk as a back-up boot environment.

8. The computer program product of claim 7 further including computer executable instructions that, when executed by the computer, configures the computer to perform the step of re-establishing the mirrors between the secondary boot disk and the primary boot disk.

9. The computer program product of claim 7 further including computer executable instructions that, when executed by the computer, configures the computer to perform the steps of:
creating a bootable boot environment on the secondary boot disk;
booting the boot environment on the secondary boot disk;
deleting an original boot environment of the primary boot disk;
designating the primary boot disk as part of a root disk group;
renaming the primary boot disk; and
mirroring the secondary boot disk to the primary boot disk.

* * * * *